United States Patent [19]

Lefrancier et al.

[11] 4,401,659
[45] Aug. 30, 1983

[54] MURAMYL-PEPTIDES FIXED TO PEPTIDE-POLYMERS AND PHARMACEUTICAL COMPOSITIONS CONTAINING THEM

[75] Inventors: Pierre Lefrancier, Bures sur Yvette; Monique Parant, Paris; Françoise Audibert, Neuilly sur Seine; Louis Chedid; Jean Choay, both of Paris, all of France; Michael Sela, Rehovot, Israel; Edgar Lederer, Sceaux, France

[73] Assignee: Agence National de Valorisation de la Recherche (ANVAR), Neuilly sur Seine, France

[21] Appl. No.: 111,701

[22] Filed: Jan. 14, 1980

[30] Foreign Application Priority Data

Jan. 12, 1979 [FR] France ................................ 79 00819

[51] Int. Cl.³ ..................... A61K 37/00; C07C 103/52
[52] U.S. Cl. .............................. 424/177; 260/112.5 R
[58] Field of Search .................. 260/112.5 R; 424/177

[56] References Cited

U.S. PATENT DOCUMENTS

| | | | |
|---|---|---|---|
| 4,082,735 | 4/1978 | Jones et al. | 424/177 |
| 4,082,736 | 4/1978 | Jones et al. | 424/177 |
| 4,094,971 | 6/1978 | Chedid et al. | 424/177 |

FOREIGN PATENT DOCUMENTS

| | | | |
|---|---|---|---|
| 1155134 | 10/1963 | Fed. Rep. of Germany | 424/177 |
| 2655500 | 12/1976 | Fed. Rep. of Germany | 424/177 |
| 2358159 | 7/1976 | France | 424/177 |
| 7413855 | 10/1974 | Netherlands | 424/177 |

OTHER PUBLICATIONS

Lefrancier, et al., Chem. Abstr. 93, (1980) 95663a.
Chedid, et al., Chem. Abstr. 91, (1971) 68444g.
Yamamura, et al., Chem. Abstr. 93, (1980) 186796n.
Azuma, et al., Infection Immunity, 1976, 18–27, vol. 14.
Kotani, et al., Biken Journal 20, (1977) 5–10, 95–103.
Yamamura, et al., Gann 67, 867–877 (1976).
Audibert, et al., Cellular Immunology 21, 243–249 (1976).
Chedid, et al., Proc. Nat'l. Acad. Sci. 74, 1977, 2089–2093.
Kusumoto, et al., Tetrahedron Letters, 47, 1976, 4287–4290.
Yamamura, et al., Proc. Japan Acad. 52, 1976, 58–61.
Kotani, et al., Biken Journal 18, (1975) 105–111.
Bergey's Manual of "Determinative Bacteriology", p. 347.
Adam, et al., Biochem. and Biophys. Res. Commun. 72, 1976, pp. 339–346.

*Primary Examiner*—Delbert R. Phillips
*Attorney, Agent, or Firm*—Weiser, Stapler & Spivak

[57] ABSTRACT

A polymer of peptidic type formed by a chain formed from aminoacyl residues preferably derived of at least one of the amino-acid residues selected from the class consisting of α,γ-diaminobutyric acid, ornithine, lysine, homo-lysine, of which the lateral amino functions portionally carry peptide branches of which the aminoacyl residues are preferably derived of those selected from the class consisting of alanine, glycine, α-aminobutyric acid, valine, leucine and proline, the above-said peptide polymer having an average molecular weight comprised between about 50,000 and 250,000, and to which are bound covalently, muramyl-peptide units of which the two first aminoacid residues bound to the muramyl group are stereoisomers of the D series, the second aminoacid residue having the structure of the glutamic acid.

This product is useful as anti-infectious agent.

30 Claims, No Drawings

MURAMYL-PEPTIDES FIXED TO PEPTIDE-POLYMERS AND PHARMACEUTICAL COMPOSITIONS CONTAINING THEM

The invention relates to novel compounds endowed with biological and pharmacological properties of great value, and notably, among these products, those which have regulating properties on the immune mechanisms.

The invention also relates to the uses of these novel products, as well as the compositions specially adapted to their application.

It is known that considerable efforts have been devoted for a long time of the research for agents endowed with regulatory properties on immune reactions. These researches have led first to the preparation of natural extract products notably fragments of peptidoglycans of the walls of mycobacteria, then to synthetic products with relatively small molecules. A series of products with very interesting properties has thus become available.

In the course of these researches, at the same time as these novel products, new properties have appeared and, in the same way, new possibilities of utilization. In return, the necessity was felt of finding products which respond better to the uses arising from the applications of these novel properties, whether to facilitate to the maximum one or several types of activity, or because it was desired to divide the different possible activities to have products available with very specific action, or again because it was desired to reduce or eliminate certain undesirable side effects.

To reach these objectives, it was necessary to modify certain forms of administration, but research has especially been undertaken to modify the activity of the compounds concerned by varying certain elements in their structure. Also, it is still of great importance to be able to have available novel products enabling the combinations of available properties to be diversified in the field of immunoregulation and, consequently, to widen the choice of the user and to adapt it better to the intended use. It is in this sense that the researches which resulted in the invention were undertaken.

Among the modifications of activity sought, one relates to extending the period of activity of the products administered by reducing their speed of elimination.

Applicant has in fact observed that products like N-acetyl-muramyl-L-alanyl-D-isoglutamine are eliminated relatively rapidly, perhaps by reason of their low molecular weight.

Another desired modification was optionally the possibility of directing the immunoregulator substance to predetermined receptor sites of the host to whom it is administered, thus leading notably to an improved effectiveness for a lower administered dose.

Another object of the invention was to possibly enable the establishing of new pharmacological properties or combinations of these properties, or again their increase to a level not hitherto obtained. With this in view, it was particularly desirable to have available products whose therapeutic index, that is to say the ratio of the effective doses to the limiting doses for which undesirable phenomena start to appear, should be as large as possible.

The improvements and modifications desired have been achieved, at least in part, by products forming the subject of the present invention.

These products comprise polymers of peptidic nature of which one chain hereafter designated as "main chain" is formed of aminoacyl residues or units corresponding to at least one of the following amino-acids: $\alpha\gamma$-diaminobutyric acid, ornithine, lysine and homolysine. Preferably, these aminoacyl residues are of the L-series. The peptidic polymer may further comprise additional chains of peptidic nature attached to the main chain through the amine functions of the aminoacyl residues of the main chain which are not engaged into the formation of that main chain. Preferably the aminoacyl units of the attached or branched chains correspond to at least one of the following acids: alanine, glycine, $\alpha$-aminobutyric acid, valine, leucine, isoleucine and proline. On the amine functions of the above-defined polymeric structure (and which are not engaged in the formation thereof) are fixed in covalent manner muramyl-peptide groups (or their homologues or derivatives as defined hereafter) in which the first aminoacyl residue of the peptide chain attached to the muramyl group (or derivative thereof) is derived from an amino-acid of the D-series (dextrorotatory stereo isomer). The second aminoacyl residue linked to the first one is derived from the D-glutamic acid. The abovesaid fixation in covalent manner brings into play one of the carboxyl functions, preferably the $\gamma$-carboxyl function of the glutamyl residue.

The polymer bearing these muramyl-peptide groups has an average molecular weight which can vary for instance between 50,000 and 250,000. Preferably the total ratio of the number of aminoacyl residues contained in the branched chain with respect to the number of aminoacyl residues contained in the main chain ranges from 1/1 to 1/30, notably from 1/10 to 1/30.

Peptide polymers of the type forming the subject of the present invention but not including muramyl-peptide groups have been described previously. These polymers have been studied as synthetic antigen carriers.

In addition, glycopeptide compounds of the muramyl-peptide type in which the two first amino-acids are of the D series have been described previously, notably in the French patent application No. 75 30948. Contrarily to what was known of the properties of N-acetyl-muramyl-L-alanyl-D-isoglutamine, it was shown, in this patent application, that the corresponding stereo-isomer, in which the amino-acids were of the D-series, did not have any specific immunostimulant property. This same compound does not stimulate non-specific immunity either, as is indicated by CHEDID et al., Prec. Nat. Acad. Sci. N.Y., 1977, 74, 2089. In other words, this compound does not facilitate the production of antibodies against the conjointly administered antigen.

Taking that art into account nothing would thus have suggested resorting to muramyl-peptides of the D-series to produce products having properties stimulating specific or non-specific immunity. In particular, it was quite impossible to foresee that the product resulting from the fixation of a compound like N-acetyl-muramyl-D-alanyl-D-isoglutamine to a peptide polymer would have remarkable anti-infectious activity, as evidenced by the pharmacological tests of the products presented in this application. Applicants have thus discovered that the muramyl-peptide products derived or similar to Mur-NAc-D-Ala-D-isoglutamine, when they are fixed to a polymer support of peptide nature of the type concerned, could show advantageously modified activity.

Preferably, to facilitate the pharmaceutical use of the compound according to the invention, those are selected whose structure is such that they can be metabolised by the organism of the host to which they are administered. In this sense, it is preferable for a part at least of the aminoacyl residues constituting the peptide polymer to be of the L series.

It is advantageous, although not indispensable, for the compounds according to the invention to be water-soluble. For this reason, it is advantageous to use a polymer having branchings and of which these branches are formed from aminoacyl links belonging to both the L and D series. It seems in fact that the simultaneous presence of these two forms, in breaking the regularity of structure of the branched chains, favours the hydrophilic character of this polymer. It is advantageous for the production of these branched chains to use a starting racemic mixture of L-alanine and D-alanine. Of course, the use of non equal proportions of L-alanine and D-alanine for producing said branched chains would not escape the spirit and the scope of the invention herein defined.

Preferred peptide polymers for the present invention are those whose principal peptide chain is formed from a L-lysine polymer.

In the same way, preferred peptide polymers are those whose branched chains are constituted by alanyl residues of the D and L series, and by prolyl residues of the L series.

A most preferred product of the invention comprises an L-lysyl polymer carrying branches constituted by polymerised chains including D-alanyl and L-alanyl (D-L alanyl) residues. Preferably, the peptide polymer has an average molecular weight of about 80,000 and the ratio of the total number of L-lysine residues of the chain to the D-L alanine residues of the branches is comprised between 1/10 and 1/30.

Advantageously, the muramyl-peptide groups fixed to the peptide polymers are such that the structure of the compounds according to the invention correspond to the following general formula

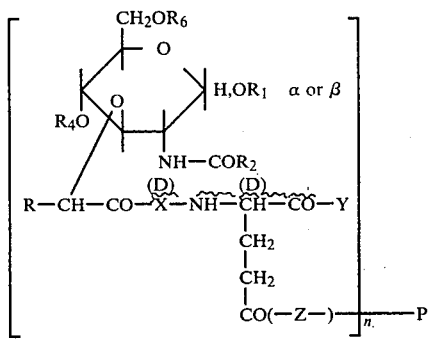

in which P represents the abovesaid polymer structure on which the glycopeptide unit is fixed and the substituents R, $R_1$, $R_2$, $R_4$, $R_6$, X, Y, and Z have the following meanings:

R is either a hydrogen atom, or an alkyl group comprising from 1 to 4 carbon atoms, $R_1$ is a hydrogen atom or an alkyl group having at the most 4 carbon atoms, or a simple or substituted aryl or alkyl-aryl group containing at the most 10 carbon atoms, $R_2$ is an hydrogen atom or an alkyl, aryl or alkyl-aryl group optionally substituted and including at the most 22 carbon atoms, $R_4$ is an hydrogen atom or an acyl radical comprising at the most 4 carbon atoms, $R_6$ is a hydrogen atom, a saturated or unsaturated acyl group, possibly branched, containing from 1 to about 90 carbon atoms and optionally carrying additional functional groups selected from the class consisting of hydroxyl, carboxyl, amino, cyclopropane and methoxyl, X is an aminoacyl residue of the (D) series, advantageously selected from the class consisting of alanyl, arginyl, asparagyl, aspartyl, cysteinyl, glutaminyl, glutamyl, histidyl, hydroxyprolyl, isoleucyl, leucyl, lysyl, methionyl, ornithyl, phenylalanyl; prolyl, seryl, threonyl, tryptophanyl, tyrosyl and valyl, Y is either —OH, or an alkoxy radical comprising from 1 to 10 carbon atoms, or an —$NH_2$ group, of which one or the two hydrogens are optionally substitutable by alkyl residues comprising from 1 to 10 carbon atoms, Z can be present or not in the formula and, when present, comprises from 1 to 3 L or D identical or different aminoacyl residues, particularly any of those of the group defined for X or glycyl, and n is a non-nil number whose value is not more than the number of amine functions carried by the polymeric structure P (notably in correspondence with number n−1 of lysyl groups contained in the main chain when the latter is polylysine.

In this formula, the second aminoacyl group of the peptide chain linked to the muramyl type group is the D-glutamyl residue. The first aminoacyl group (denoted by X) is selected from among the different aminoacyl residues of the D-series mentioned above. Among the compounds of formula I, those are preferred in which the first aminoacyl group is D-alanyl. A second type of preferred compounds are those in which this aminoacyl is D-seryl.

The compounds in which the first aminoacyl group is D-prolyl, D-threonyl or D-valyl are also advantageous.

Between the D-glutamyl residue and the peptide polymer chain there may be inserted one or several additional aminoacyl residues denoted in the general formula by Z.

Preferably, these aminoacyls are selected from among the group consisting of alanyl, leucyl, glycyl, valyl and isoleucyl.

The number of aminoacyls between the D-glutamyl and the chain P can vary from 0 to 3, preferably however it is either 0, or 1 or 2.

In the α position of the D-glutamyl residue, the possible variations or substitutions are represented by Y. Y can first be an —$NH_2$ radical, of which one at least of the hydrogen atoms is optionally substitutable by short alkyl residues comprising from 1 to 10 carbon atoms. Y may also be an alkoxy, particularly one comprising from 1 to 10 carbon atoms.

In a preferred embodiment, Y is —$NH_2$.

Other preferred products are those wherein Y is either —$OCH_3$, or $OC_4H_9$, or $OC_{10}H_{21}$.

In the most preferred products $R_2$ is $CH_3$, $R_1$, $R_4$ and $R_6$ are hydrogen atoms and R is —$CH_3$ (groups of the N-acetyl-muramyl structure). In another preferred form, the R group is a hydrogen; the corresponding groups then show the structure of the lower homologue denoted by the name N-acetyl-nor-muramic acid. Finally, in another preferred form, R is —$C_2H_5$ (so-called N-acetyl-homo-muramic structure).

The hydroxyl borne by the anomeric carbon in the saccharide groups of the product according to the invention can be in α or β form. This oside residue can also carry different substituents of which the prior art, relating to adjuvant agents of the muramyl-peptide type, has given a certain number of examples. In particular, the literature describes products in which ester or ether groups are substituted for the hydroxyls of the oside moiety or alkyl groups for the hydrogen of the NH radical in the 2-position.

In the general formula of the products according to the invention, the substituents of the glucopyranoside ring have been denoted by $R_1$, $R_2$, $R_4$ and $R_6$. The various positions do not have the same possibilities of substitution, the 6 position being that for which the greatest latitude is offered.

Preferred compounds are those in which one or several of the substituents $R_1$, $R_4$ and $R_6$, independently of one another or simultaneously, are hydrogen.

Advantageous compounds are also those for which $R_4$ is the acetyl group.

Preferred compounds are also those for which $R_6$ is an acyl radical containing from 1 to 4 carbon atoms, and notably the acetyl radicals (—$COCH_3$), or again those for which $R_6$ is the mycolyl group (about $C_{80}$ to $C_{90}$) or corynomycolyl ($C_{32}$).

Preferred $R_2$ substituents are constituted by the alkyl groups comprising from 1 to 4 carbon atoms, preferably —$CH_3$.

Among the compounds according to the invention those are particularly preferred for which $R_1$, $R_4$, $R_6$ are simultaneously a hydrogen atom, R and $R_2$ are —$CH_3$, X is D-alanyl, Y is —$NH_2$.

The products according to the invention are prepared by synthesis or, if necessary, by hemisynthesis. In a first stage, the glycopeptide derivative is synthetised, then in a second stage, it is fixed in covalent manner on the polymer peptide chain using one or other of the known coupling methods.

The modes of preparing muramyl-peptides have been described in the literature for a certain number of them. For convenience, general methods of preparation for these products are indicated below. Of course, these methods are not the only ones which can be contemplated, and numerous modifications may also be used.

To arrive at a glycopeptide compound, various routes are possible. In all cases, synthesis includes a series of steps in the course of which the various "fragments" constituting the whole structure of the compounds according to the invention is progressively assembled. The principal differences between the possible routes are found in the sequence selected for assembling the fragments. The reaction methods leading to the fixing of one fragment to the contiguous fragment (or preassembled fragments) are as a matter of principle little modified by the order in which this synthesis is conducted, to the extent, of course, that this order depends, on the one hand, on the choice of the functional groups which react and which, consequently, must be free and available for the step concerned, and on the other hand, the choice of the group which must be blocked (or protected) in order not to interfere in the course of this same step.

Preparation of the products according to the invention can be done from the corresponding compounds of the muramyl-peptide type. The production of the latter has been described in numerous publications. Optionally, for those whose preparation does not appear expressly in the literature, and notably for the various modifications corresponding to the substitutions of the muramyl group or of the analogous group, they may be obtained by following the traditional methods of preparing corresponding derivatives in oligosaccharide chemistry. In the same way, the constitution of the peptide chain bound to the muramic acid is carried out according to the traditional methods in peptide synthesis.

Below are given succinctly the principal indications relating to the different operations which can be brought into use for synthetising the products according to the invention, first by envisaging each step separately, then by indicating some preferred type sequences.

(a) Formation of muramic acid or of the analogues

To obtain the analogues of N-acetyl-muramic acid of the formula

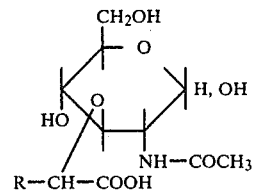

in which R has the previously indicated meaning, it is possible to start from a derivative of N-acetyl-2-deoxy-glucosamine whose hydroxyls in 1, 4 and 6 positions are blocked by conventional methods. The method of preparing such a derivative, benzyl-2-acetamido-4, 6-O-benzylidene-2-deoxy-D-glucopyranoside, is described notably by P. H. GROSS and R. W. JEANLOZ (J. Org. Chem., 1967, 32, 2761).

The formation of N-acetyl-muramic acid (R=$CH_3$) or of one of its analogues such as N-acetyl-nor-muramyl acid (R=H) can be conducted in the manner described in French patent application Nos. 74 22909 or 76 19236 and by OZAWA and JEANLOZ (J. Org. Chem., 1965, 30, 448).

This formation comprises for example the preparation of a sodium salt of the hydroxyl in the 3 position and the subsequent condensation of the sodium derivative with the salt or the ester of a halogenated acid such as 2-chloro-propionic or chloroacetic acid, as disclosed in the two previously mentioned patent applications. The halogenated compound of the L form used may be prepared according to the method described by SINAY and al (J. Biol. Chem., 1972, 247, 391). By using suitable halogenated acids, it is possible to prepare all the derivatives corresponding to the various meanings of R. THUS, to introduce a group R with 4 carbons, there may be used the salts or esters of 2-chloro-butyric acid.

When an ester of a halogen acid is used, the carboxylic function may be freed by suitable hydrolysis, in order to be able to proceed with the subsequent peptide condensation.

(b) Substitution on the saccharide residue

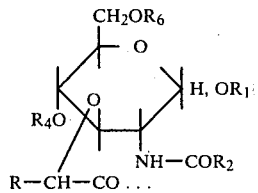

Starting from the N-acetyl-muramic derivatives blocked in the 1, 4, 6 positions, as obtained in (a), it is possible to prepare the various analogous compounds in which the acetyl group fixed on the nitrogen in the 2 position is replaced by substituents whose nature is that given in the general definition, that is to say an alkyl, aryl or alkyl-aryl group possibly substituted and including at the most 22 carbon atoms. For this modification, it is possible to operate in known manner a hydrolysis of the acetyl by a strong base, for example as this is described in the publication of P. H. GROSS and JEANLOZ indicated above.

The resulting compound, in which an amino group is in the 2 position of the glucopyranoside ring, can then again be subjected to an acylation treatment, under conventional conditions, with a suitable acylating agent corresponding to the desired group $R_2$. As acylating agent, may be used notably acid-anhydrides or -chlorides.

The substitutions at the 1, 4 and 6 positions may be effected by methods which have been described previously and which are traditional in sugar chemistry. When the substituents envisaged are different from one another, as many successive substitution reactions follow as there are separate substituents. In the course of these reactions, the positions must not be substituted or those which must be subsequently the subject of another substitution are protected temporarily by blocking groups by the usual methods.

The blocking groups initially present, in the case where one starts, as previously indicated, from benzyl-2-acetamido-4,6-O-benzylidene-2-deoxy-D-glucopyranoside, are removed for example under the action of acetic acid (60% refluxing for one hour) and catalytic hydrogenation, as described for example by MERSER et al (Biochem. Biophys. Res. Commun., 1975, 66, 1316), or by catalytic hydrogenation by the method of LEFRANCIER et al (Int. J. Peptide protein Res., 1977, 9, 249).

The methods of substitution are those traditionally used. To obtain the acylated derivatives, an acylating agent is used corresponding to the desired substituent (anhydride, acyl chloride, etc.).

The 1,4, 6 positions are not equivalent as regards reactivities. The C-6 position is the easiest to substitute. Thus, when only this position must be substituted, it is possible to operate without blocking the other positions, with an amount of substitution agent equivalent to that necessary for the substitution of a single position.

A particular example of the method of preparing derivatives substituted at the 6 position is given in an article of KUSUMOTO et al (Tetrahedron Letters, 1976, 47, 4237).

The substitutions on the oside residue can be carried out before or after the fixing of the peptide chain or of the fragments of the latter.

(c) Peptide chain

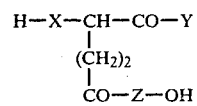

The fixing of a peptide chain to the N-acetylmuramic acid, or to an analogue of the latter, such as those which have been indicated above, is obtained by conventional methods in the field of peptide synthesis. Such methods have been amply described in the prior art and in particular in the previously indicated French patent applications.

In general, the glycopeptide synthesis can be done either by fixing a first aminoacid to the muramyl group, then by fixing the second aminoacid to the compound thus obtained, and so on step by step. It is also possible to prepare the whole peptide chain separately aminoacid by aminoacid and to fix the latter to the muramyl group. It is finally possible to select intermediate processes in which fragments of the chain are prepared, then either to assemble these fragments together until the complete chain is formed which is then fixed to the muramyl group, or to fix a first fragment to the muramyl group, then a second to the product thus obtained, etc. The choice of the sequence is guided principally by reasons of convenience or yield.

The Y substitution is advantageously carried out on the glutamyl group before the synthesis of the chain.

The peptide synthesis is carried out by conventional methods. By way of example, it is possible to utilise carboxyl activation methods, like the so-called "mixed anhydride method". Advantageously, the peptide synthesis is carried out by means of a compound of the carbodiimide type such as N, N'-dicyclohexylcarbodiimide or equivalent carbodiimides. A review of traditional peptide synthesis methods is to be found in J. H. JONES, Chemistry and Industry, 723 (1974). It is also possible to refer to the following French patent application Nos.: 75 29624, 76 06819, 76 06820, 76 06821, 76 21889, 77 02646, and to the article of LEFRANCIER et al (Int. J. Peptide Protein Res., 1977, 9, 249).

The formation of esterified or amidated derivatives corresponding to the Y group is obtained in known manner. It is possible in particular to refer to the above-indicated French patent applications, and notably to application Nos. 76 06820, 76 06821, 76 21889 and 77 02646.

The diagram represents the reaction sequences leading to the production of glycopeptide derivatives which will then be coupled to the peptide polymer chain. One starts from a derivative (1) with $R_1$ benzyl radical, described by GROSS and JEANLOZ (J. Org. Chem., 1967, 32, 2759). To obtain the corresponding compound in which $R_1$ is an alkyl or aryl-alkyl group, it is possible to use the method of preparation of the corresponding α or β-glycoside also described in this same article, or any known method for such preparations in oligosaccharide chemistry.

If it is desired to modify the nature of the N-acyl group, the N-acetyl group may be hydrolysed as described again by GROSS and JEANLOZ, to result in derivatives of formula (2). The derivatives (2) can then be N-acylated selectively by the action of carboxylic acid anhydrides to result in derivatives of formula (3). The derivatives of formula (4) may be obtained from the preceeding ones by the method described by OZAWA and JEANLOZ (J. Org. Chem., 1965, 30, 448), by means of an L-α-chloroalkanoic acid.

The derivatives of formula (4) are coupled with a peptide derivative of the general formula H-X-D-Glu-(Z-OBzl)-OXY-hydrochloride, in which formula X corresponds to an amino acid, and Y for example to an amino-, methylamino-, methoxy- or glycyl-amide radical. These various peptide derivatives are prepared by the methods described by LEFRANCIER et al (Int. J. Peptide Protein Res., 1977, 9, 249, and Int. J. Peptide Protein Res., 1978). The coupling methods used to obtain the glycopeptide derivatives of formula (5) are also described in the previously mentioned articles. However, both in the synthesis of dipeptide derivatives and in that of derivatives of formula (5), any coupling method used in peptide synthesis may be applied.

The catalytic hydrogenation of the compound of formula (5) is carried out conventionally (LEFRANCIER et al, Int. J. Peptide Protein Res., 1977, 9, 249) to result in compounds of formula (6).

The derivatives of formula (6) are coupled, for example by the method described below in detail, by means of a water-soluble carbodiimide and hydroxy-benzotriazole, with the peptide polymer chain. Compounds of formula (7) are obtained.

In a modification, the derivatives of formula (5) undergo a selective debenzylidenation as described by MERSER et al (Biochem. Biophys. Res. Commun., 1975, 66, 1316) to give the derivatives of formula (8). The selective acylation of the primary hydroxyl in the 6 position of the saccharide residue can then be done directly by the action of a slight excess of carboxylic acid anhydride or of acyl-imidazole. Derivatives of formula (9) are obtained.

The derivatives of formula (9) may be synthetised by a totally different sequence (Diagram II, formula 4) similar to that developed by KUSUMOTO et al (Tetrahedron Letters, 1976, 47, 4237).

After catalytic hydrogenation of compounds (9), carried out as usual in the presence of 5% palladium on charcoal, compounds of formula (10) are obtained to which, as previously, may be coupled a residue to give the compound (11) according to the invention.

In another modification, the derivatives of formula (8) are diacylated on the two hydroxyls in the 4 and 6 positions of the saccharide residue by the action of an excess of carboxylic acid anhydride, then subjected to catalytic hydrogenation carried out as usual in the presence of 5% palladium on charcoal, to obtain compounds of formula (13). After coupling with the peptide polymer chain as previously, the compounds (14) according to the invention are obtained.

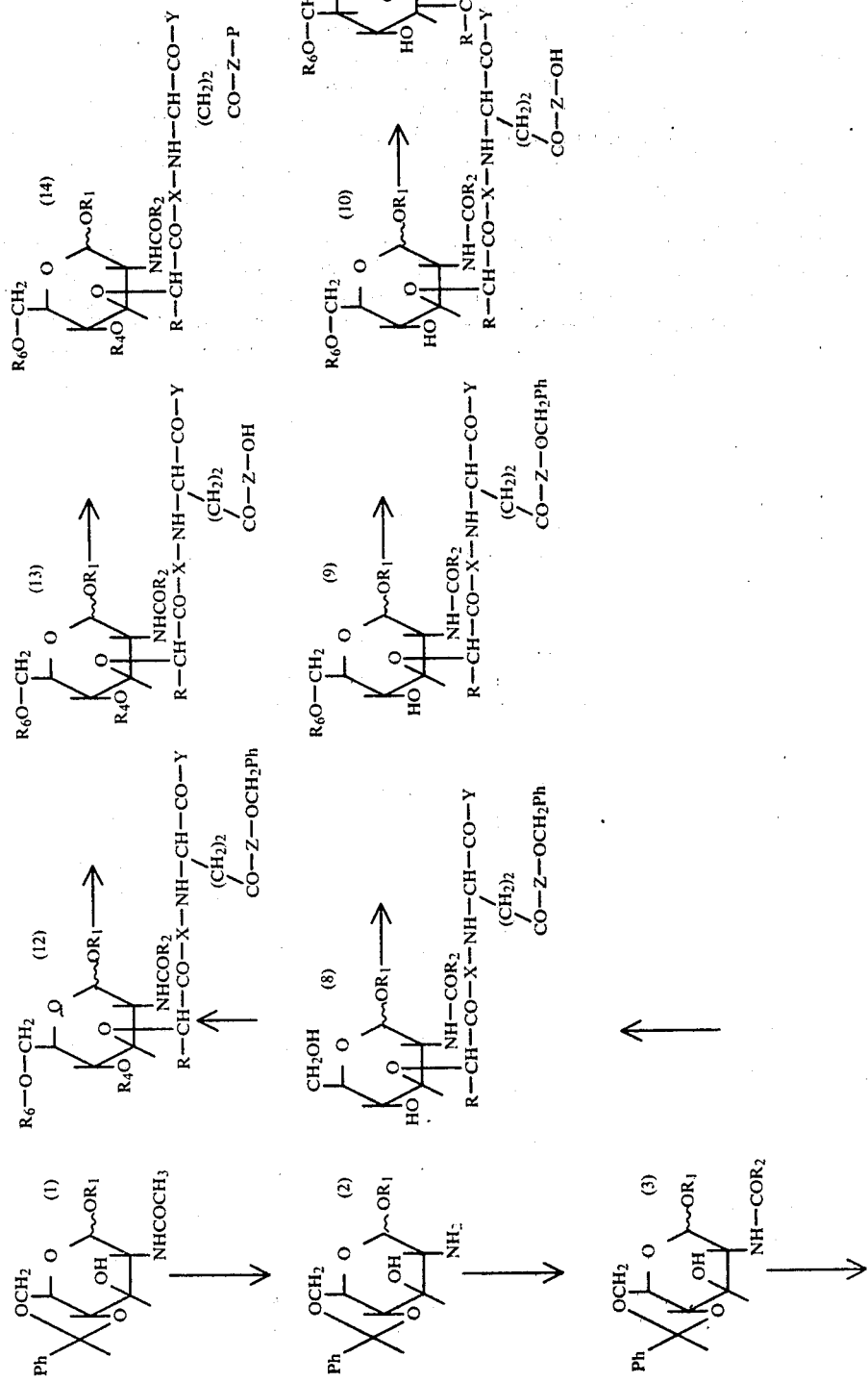

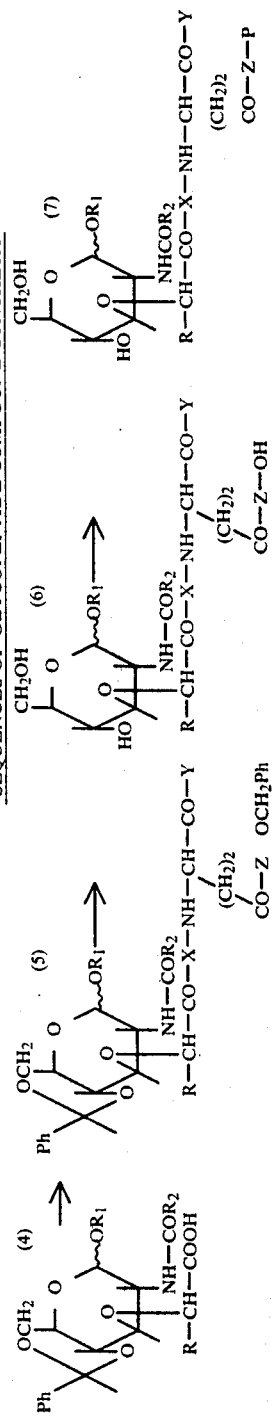
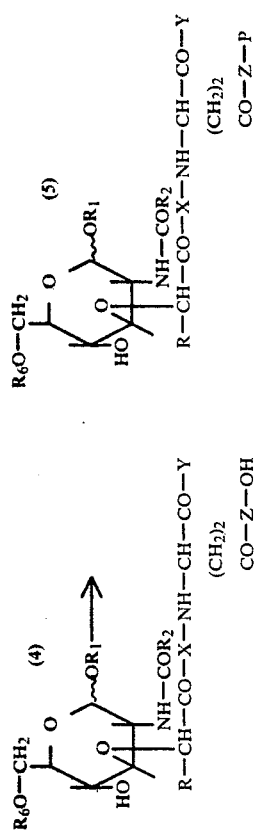
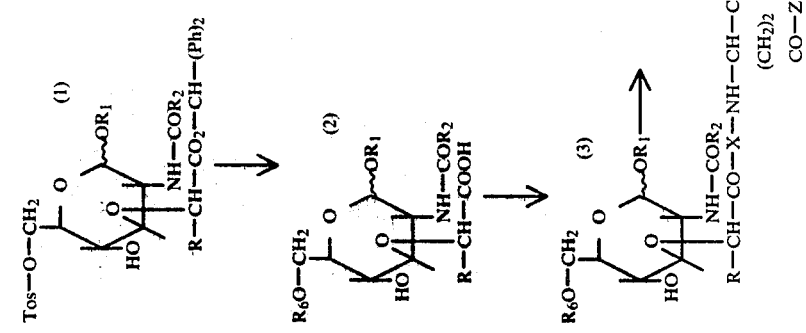

The invention also relates to methods of using the compounds corresponding to the foregoing definitions, notably as a reagent or as an active substance in pharmaceutical compositions.

The invention relates to the standardized biological reagents which can be constituted by means of the compounds according to the invention, notably in order to study the possible anti-infectious properties of substances being investigated, by comparison with such standard reagents.

More particularly, the invention relates to medicaments or pharmaceutical compositions including as active principle at least one of the compounds according to the invention in association with a pharmaceutical vehicle particularly suitable for the control of the immune response in the host to which it is administered.

These pharmaceutical compositions are notably useful for the treatment of infectious diseases of bacterial or parasitic origin, or the inhibition of tumoral disorders. Particularly effective doses of the pharmaceutical compositions including the compounds according to the invention may be used for the treatment of infections caused by agents resistant to antibiotics and more generally for the stimulations of the defenses of the organism of the host against pathogens.

The application of these medicaments is not only curative; it may also be preventive.

The medicaments according to the invention may be administered to the host—animal or human being—in any suitable manner for the production of the desired action.

The invention relates naturally also to various compositions in which the compounds according to the invention may be incorporated, optionally in association with other active substances.

Advantageous pharmaceutical compositions are constituted by injectable solutions or suspensions containing an effective dose of at least one product according to the invention. Preferably, these solutions or suspensions are formed in an isotonic sterilised aqueous phase, preferably saline or glucosed.

The invention relates more particularly to such suspensions or solutions which are adapted to be administered by intradermal intramuscular or sub-cutaneous injections, or again by scarification.

Other advantageous pharmaceutical compositions are constituted by liposome forms of the compounds according to the invention. As is known, the liposomes, by reason of the lipid nature (and notably phospholipid nature) of the elements entering into their composition, constitute, for certain cases, a particularly suitable presentation.

The invention also relates to pharmaceutical compositions administrable by other routes, notably by the oral or rectal route, or again in forms intended to come into contact with the mucous membranes notably the ocular, nasal, pulmonary or vaginal mucous membranes.

Consequently, it relates to pharmaceutical compositions in which one at least of the compounds according to the invention is associated with pharmaceutically acceptable excipients, solid or liquid, adapted to the constitution of oral, ocular or nasal forms, on which excipients adapted to the constitution of forms for rectal administration, or again with excipients adapted to vaginal administration, for example gelatinous. It relates lastly to compositions designed for the pulmonary route, notably solutions prepared for administration by means of a conventional aerosol device.

The invention also relates to a process aimed at reinforcing the immune defences of the host, consisting in administering to the host an effective dose of one at least of the products according to the invention, in one of the forms of administration which have been discussed above. By may of example of doses which can induce an action, may be mentioned doses of 10 to 1000 $\mu$g per kg of body weight, for example 50 $\mu$g, when the administration is done by the parenteral route, or again a dose of 200 to 20,000 $\mu$g per kg of body weight, for example 1000 $\mu$g, for other forms of administration, such as, for example, the oral route.

The invention is described in more detail in the examples which follow relating to the preparation of the product according to the invention, and to various trials concerning the pharmacological properties of this product.

Preparation of the supporting peptide polymer (A--L) or multi-poly (DL-alanyl)-poly(L-lysine) anhydride and poly-L-lysine.

A 300 ml solution of a 0.05 mole/liter phosphate buffer corresponding to a pH of 7 containing 1 gram of poly-L-lysine hydrobromide was placed in a round-bottom flask. The flask was cooled to about 2° C. in an ice bath. 14 g of DL-alanine anhydride in solution in 200 ml of anhydrous dioxane were added under vigorous stirring. A considerable evolution of $CO_2$ was observed.

The flask was kept in the ice bath with stirring overnight. The solution recovered was dialysed several times against distilled water to remove the low molecular weight constituents; then it was freeze-dried.

To achieve purification, it is possible after dialysis also to subject the solution obtained to gel-filtration, for instance on a column of the gel available in the trade under the designation SEPHADEX.

Preparation of multi-[poly-(N-acetyl-muramyl-D-alanyl-D-isoglutaminyl)-D,L-alanyl]-poly-L-lysine (abbreviated as MDP (D-D) (A--L))

675 mg (1.35 mmole) of N-acetyl-muramyl-D-alanyl-D-isoglutamine were dissolved in 12.5 ml of dimethylformamide. To this solution were successively added 187.5 mg of hydroxy-benzotriazole and 575 mg of N-ethyl-N'-(dimethylaminopropyl)-carbodiimide, hydrochloride. After 1 hour, this reaction mixture was added to an aqueous solution (25 mg) with 250 mg of previously prepared peptide polymer (corresponding to 135$\mu$ equivalents of theoretically available amine functions) adjusted to pH 8.5 with a molar solution of $NaHCO_3$.

The reaction continued for 24 hours. 80 ml of water were then added and the product was obtained after freeze-drying. It was redissolved in 50 ml of water, ultrafiltered on an Amicon PM 10 filter and finally obtained after freeze-drying and dessication. In this way 226 mg of the product according to the invention were obtained.

The product obtained was analysed as follows. An aliquot fraction (1 mg) was hydrolysed (6 NHCL, 24 h at 110° in sealed tube under vacuum), then and amino acid analysis followed: muramic acid—380, glutamic acid—430, alanine—11 463, lysine—450.

Based on the results of the glutamic acid and the lysine, the yield obtained was 95.5%, and the molar ratio was MDP (D-D)/Lys/Ala: 0.64/1/21, namely again 0.211 mg of MDP (D-D) per mg of MDP(D-D)-AL.

PHARMACOLOGICAL PROPERTIES

The results shown below relate to a product of the type according to the invention. Systematically, in these trials, this product according to the invention was compared with the corresponding glycopeptide, not fixed on the peptide polymer. To facilitate the comparison, the amount of glycopeptide contained in the doses tested of the product according to the invention are indicated.

To simplify the record, the following abbreviations are used:

MDP(D-D): N-acetyl-muramyl-D-alanyl-D-isoglutamine (A--L): polymer formed by an L-lysine chain with D-L-alanine branches MDP(D-D)(A--L): N-acetyl-muramyl-D-alanyl-D-isoglutamine fixes on the (A--L) polymer.

(1°) Anti-infectious activity with respect to Klebsiella

The testing procedure is described in the article of CHEDID L. and Col., Proc. Natl. Acad. Sci. USA, 1977, 74, 2089.

In this way, there was established previously an experimental method enabling the anti-infectious character of the products to be demonstrated. It was shown that a dose of about $10^4$ Klebsiella pneumoniae, injected by the intramuscular route in mice, results in the progressive death of a considerable part, if not the whole, of the animals in the week following the inoculation. After eight days, the survival of the animals was definitely achieved.

The survival of groups of mice inoculated under the above-indicated conditions and treated by means of the products according to the invention, was recorded.

For these trials, hybrid mice (C57Bl/6 x AKR)F1 raised in the PASTEUR INSTITUTE, from strains derived from the C.N.R.S. breeding station at ORLEANS were used.

The infection by Klebsiella pneumoniae, a strain of the 2-capsular type, biotype d, was done from a culture of 16 hours in a medium for pneumococci (No. 53515, INSTITUT PASTEUR). The infecting dose was $1.5.10^4$ Klebsiella; it was administered by the intramuscular route.

The administration of the tested product was carried out by the intravenous route in 0.2 ml of apyrogenic physiological solution, the controls receiving the solution alone. It was carried out 24 hours before the inoculation.

The results of these trials are reported in the following Table. The percentage of protection indicated is the difference in the percentages of survivors of the treated group with respect to the control group.

| i.v. treatment at D − 1 | Doses+ (μg) | Number of mice | Number of survivors at D + 3 | D + 5 | D + 8 | Percentage of protection |
|---|---|---|---|---|---|---|
| Controls | — | 32 | 16 | 7 | 4 | — |
| MDP(D-D) | 100 | 30 | 21 | 12 | 7 | 6 |
| | 1000 | 16 | 6 | 4 | 4 | 9 |
| MDP(D-D)(A--L) | 1 | 24 | 15 | 7 | 6 | 9 |
| | 10 | 32 | 26 | 19 | 17 | 38 |

+doses expressed in weight of glycopeptide

These results show a profound difference in the properties of the glycopeptide according to whether it is fixed or not on the polymer. Even at high doses, the MDP(D-D) alone is practically not anti-infectious, although the anti-infectious activity of the product according to the invention is very substantial even at relatively low doses.

Similar trials were carried out on young mice of 7 days which had a very great sensitivity to infection by Klebsiella, as indicated by M. PARANT et al (Proc. Acad. Sci. N.Y., 1978, 75, 33-95).

In these trials, the product studied was administered, by the sub-cutaneous route, 24 hours before the infecting test. For the latter, the infecting dose was $1.2.10^3$ Klebsiella; it was also administered by the sub-cutaneous route.

| s.c. treatments at D − 1 | Doses (μg) | Number of mice | Number of survivors at D + 3 | D + 5 | D + 8 |
|---|---|---|---|---|---|
| Controls | — | 53 | 5 | 1 | 0 |
| (A--L) | 50 | 40 | 20 | 7 | 0 |
| MDP(D-D) | 10 | 10 | 0 | 0 | 0 |
| | 100 | 16 | 3 | 0 | 0 |
| MDP(D-D)(A--L) | 1 | 39 | 19 | 6 | 3 |
| | 10 | 75 | 50 | 28 | 18 |

The results of these trials, for the product according to the invention, show a significant protection of the animals as well as a considerable delay in the mortality in animals which were not definitely protected.

(2°) Sensitisation trials

These trials were undertaken to study the possible immunogenic properties of the products according to the invention. At the same time, sensitisation tests with respect to various products were carried out.

The tests were carried out on guinea-pigs. The preparations shown in column 1 of the Table of the results were injected by the plantar route. They comprise 100 μg of the product tested incorporated in incomplete FREUND adjuvant (IFA) or in complete FREUND adjuvant (CFA).

Three weeks after this first injection, 50 μg of the products indicated in the upper portion of the Table of results were injected by the dermal route. Possible reactions were observed 48 hours later.

| | MDP | MDP (D-D) | MDP (D-D) (A--L) | (A--L) | OV |
|---|---|---|---|---|---|
| IFA + MDP | — | — | — | — | |
| CFA + MDP | — | — | — | — | |
| IFA + MDP + OV | — | — | — | — | + |
| IFA + MDP(D-D)(A--L) | — | — | — | — | |

| | MDP | MDP (D-D) | MDP (D-D) (A–L) | (A–L) | OV |
|---|---|---|---|---|---|
| CFA + MDP(D-D)(A–L) | — | — | — | — | |
| IFA + MDP(D-D)(A–L) + OV | — | — | — | — | — |

These results show notably that MDP(D-D) (A–L) does not elicit a sensitivity reaction neither with respect to itself, nor with respect to adjuvant agents like MDP, and is not adjuvant to specific immunity when it is administered with ovalbumin. The same observation was made for the product administered in isotonic saline solution with albumin of bovine serum.

(3°) Study of the toxicity and of the pyrogenic effect

The toxicity of the products was studied by parenteral administration in mice adrenalectomised to render them particularly sensitive to the endotoxins.

In addition, the pyrogenic doses in the rabbit were determined, that is to say the doses causing an increase in temperature equal to or higher than 0.6° C. (European Pharmacopoea, Vol. 2, 1971, pages 58–60).

It is observed that the therapeutic index is much improved. In fact, if there is a certain increase in toxicity, the latter is negligible compared with the increase in activity which is very considerable.

We claim:

1. A pharmacologically active oligomeric peptide derivative which comprises (1) a polylysyl chain P which optionally includes branched chains formed of alanyl residues attached to the chain through the amino groups of lysyl groups in the chain not linked in the forming of said chain and (2) covalently linked to amino groups not linked into said chain P, muramyl peptide groups which comprise a glucopyranoside ring and linked thereto a peptide chain which chain comprises aminoacyl residues, the first of said aminoacyl residues being of an amino acid of the D-series and the second amino acyl residue being of D-glutamic acid, said oligomeric peptide derivative having the formula:

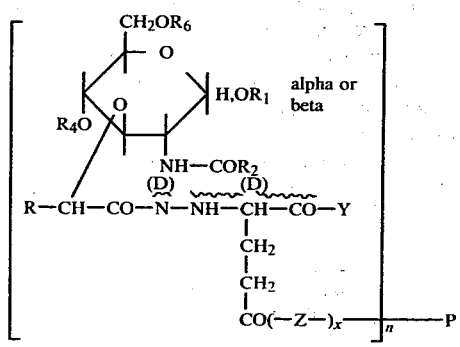

in which the substituents R, $R_1$, $R_2$, $R_4$, $R_6$, X, Y, Z, x and n are defined as follows:

R is either a hydrogen atom or alkyl group having from 1 to 4 carbon atoms, $R_1$ is hydrogen or alkyl having at most 4 carbon atoms or a simple or substituted aryl or alkyl-aryl having at most 10 carbon atoms, $R_2$ is hydrogen or alkyl, aryl or alkyl-aryl optionally substituted and having at most 22 carbon atoms, $R_4$ is hydrogen or acyl having at most 4 carbons, $R_6$ is hydrogen, a saturated or unsaturated acyl optionally branched having from 1 to about 90 carbon atoms and optionally having groups selected from the class consisting of hydroxyl, carboxyl, amino, cyclopropyl and methoxyl, X is an aminoacyl residue of the (D) series, selected from the class consisting of alanyl, arginyl, asparagyl, aspartyl, cystenyl, glutaminyl, glutamyl, histidyl, hydroxyprolyl, isoleucyl, leucyl, lysyl, methionyl, ornithyl, phenylalanyl, prolyl, seryl, threonyl, tryptophanyl, tyrosyl and valyl, Y is either —OH, or alkoxy having from 1 to 10 carbon atoms or —$NH_2$ group, of which one or the two hydrogens is optionally substituted by an alkyl having from 1 to 10 carbon atoms, Z is from 1 to 3 L- or D- identical or different aminoacyl residues, x is zero or an integer of 1 through 3, and n is a an integer other than zero, which integer is not more than the number of amino groups of chain P.

2. The oligomeric peptide derivative of claim 1 in which the chain P has branched peptide groups constituted of alanyl residues linked through the amino groups of the amino acyl residues.

3. The oligomeric peptide derivative of claim 2 in which the aminoacyl residues of the peptide groups are selected from amino acids of the group consisting of alanyl, alpha-aminobutyric acid, valyl, leucyl, isoleucyl or prolyl.

4. The oligomeric peptide derivative of claim 2 in which P consists of a polylysine chain.

5. The oligomeric peptide derivative of claim 1 in which the polymer is a L-lysyl polymer.

6. The oligomeric peptide derivative of claim 5 in which n is one integer less than the number of lysyl groups of the L-lysyl polymer.

7. The oligomeric peptide derivative of claim 1 in which the alnyl residues of the branched chains are of both the D- and L- series.

8. The oligomeric peptide derivative of claim 1 in which P includes L-polylysyl having linked thereto D- and/or L- alanyl.

9. The oligomeric peptide derivative of claim 8 in which the oligomeric peptide has an average molecular weight of 80,000 and the ratio of L-lysyl of P to the D- and L- alanyl of the branched chains linked thereto is between 1/10 to 1/30.

10. The oligomeric peptide derivative of claim 1 which has an average molecular weight from about 50,000 to about 250,000.

11. The oligomeric peptide derivative of claim 1 which is metabolizable.

12. The oligomeric peptide derivative of claim 1 wherein Y is —$NH_2$, —$OCH_3$, —$OC_4H_9$ or $OC_{10}H_{21}$.

13. The oligomeric peptide derivative of claim 1 wherein x is 1 or 2 and Z is an aminoacyl residue selected from the group consisting of alanyl, glycyl, valyle, leucyle and isoleucyle.

14. The oligomeric peptide derivative of claim 1 wherein R is —$CH_3$.

15. The oligomeric peptide derivative of claim 1 wherein $R_1$, $R_4$ and $R_6$ are hydrogen and $R_2$ is —$CH_3$.

16. The oligomeric peptide derivative of claim 9 wherein the muranyl peptide group are N-acetyl-muramyl-D-alanyl-D-isoglutaminyl.

17. The oligomeric peptide derivative of claim 1 wherein X is selected from the group consisting of D-prolyl, D-threonyl, and D-valyl.

18. The oligomeric peptide derivative of claim 1 wherein x is from 0 to 3.

19. The oligomeric peptide derivative of claim 1 wherein Y is $-NH_2$.

20. The oligomeric peptide derivative of claim 1 wherein Y is selected from the group consisting of $-OCH_3$, $-OC_4H_9$, or $-OC_{10}H_{21}$.

21. The oligomeric peptide derivative of claim 1 wherein $R_2$ is $-CH_3$, $R_1$, $R_4$ and $R_6$ are each hydrogen and R is $-CH_3$.

22. The oligomeric peptide derivative of claim 1 wherein R is $-C_2H_5$.

23. The oligomeric peptide derivative of claim 1 wherein at least one of $R_1$, $R_4$ and $R_6$ is hydrogen.

24. The oligomeric peptide derivative of claim 1 wherein $R_4$ is acetyl.

25. The oligomeric peptide derivative of claim 1 wherein $R_6$ is selected from the group consisting of acetyl of 1 to 4 carbons, mycolyl and corynomycolyl.

26. The oligomeric peptide derivative of claim 1 wherein $R_1$, $R_4$, and $R_6$ are hydrogen; R and $R_2$ are $-CH_3$, X is D-alanyl and Y is $-NH_2$.

27. The oligomeric peptide of claim 1 wherein X is D-alanyl.

28. A pharmaceutical composition for enhancing the resistance of a host against pathogens which comprises an effective amount of a biologically active oligomeric peptide derivative of any one of claims 1, 2, 3, 4, 5, 6, 7, 8, 9, 10, 11, 12, 13, 14, 15, 16, 17, 18, 19, 20, 21, 22, 23, 24, 25, 26 or 27 and a pharmaceutically acceptable carrier.

29. The method for enhancing the resistance of a host against pathogens which comprises administering to said host an effective amount of a biologically active oligomeric peptide derivative of any one of claims 1, 2, 3, 4, 5, 6, 7, 8, 9, 10, 11, 12, 13, 14, 15, 16, 17, 18, 19, 20, 21, 22, 23, 24, 25, 26, or 27 in a biologically acceptable carrier.

30. The oligomeric peptide derivative of claim 10 which is multi-poly-L-lysine.

* * * * *